(12) United States Patent
Morris (10) Patent No.: US 7,083,913 B2
(45) Date of Patent: Aug. 1, 2006

(54) HIGH THROUGH-PUT CLONING OF PROTOONCOGENES

(75) Inventor: David Morris, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 114 days.

(21) Appl. No.: 10/466,939

(22) PCT Filed: Jan. 18, 2002

(86) PCT No.: PCT/US02/01651

§ 371 (c)(1),
(2), (4) Date: Jan. 26, 2004

(87) PCT Pub. No.: WO02/057497

PCT Pub. Date: Jul. 25, 2002

(65) Prior Publication Data

US 2004/0142336 A1   Jul. 22, 2004

Related U.S. Application Data

(60) Provisional application No. 60/262,724, filed on Jan. 18, 2001.

(51) Int. Cl.
  *C12Q 1/70* (2006.01)
  *C12Q 1/68* (2006.01)
  *C12P 19/34* (2006.01)

(52) U.S. Cl. .............................. 435/5; 435/6; 435/91.2

(58) Field of Classification Search .................... 435/6, 435/91.1, 91.2
See application file for complete search history.

(56) References Cited

FOREIGN PATENT DOCUMENTS

EP    WO 02/057497 A2    7/2002

OTHER PUBLICATIONS

Valk et al., Nucleic Acids Research 25(21), 4419-4421 (1997).*
M. van Lohuizen, et al., "Identification of Cooperating Oncogenes in Eu-myc Transgenic Mice by Provirus Tagging," Cell, vol. 65, pp. 737-752 (1991).
J. Li, et al., "Leukaemia Disease Genes: Large-Scale Cloning and Pathway Predictions," Nature Genetics, vol. 23, pp. 348-353 (1999).
A. Berns, et al., "Identification and Characterization of Collaborating Oncogenes in Compound Mutant Mice," Cancer Research (Suppl.), 59, pp. 1773S-1777S (1999).
H. Jacobs, "TCR-Idepedent T Cell Development Mediated by Gain-Of-Oncogene Function or Loss-of-Tumor-Suppressor Gene Function," Immunology, vol. 12, pp. 487-502 (2000).
H. Mikkers, et al., "High-Throughput Retroviral Tagging to Identify Components of Specific Signaling Pathways in Cancer," Nature Genetics, vol. 32, pp. 153-159 (2002).
International Search Report mailed Feb. 6, 2003.
Maarten Van Lohuizen et al, Identification of Cooperation Oncogenes in Eµ-*myc* Transgenetic Mice by Provirus Tagging, Cell Magazine, May 31, 1991, 737-752, V 65, n 5, Cell Press, Cambridge, USA, (Duplicate).
Anton Berns et al, Identification and Characterization of Collabarationg Oncogenes in Compound Mutant Mice[1], Cancer Research (Suppl.), Journal, Apr. 1, 1999, 1773s-1777s, v. 59, n 7 suppl, USA, (Duplicate).

* cited by examiner

*Primary Examiner*—Kenneth R. Horlick
(74) *Attorney, Agent, or Firm*—Townsend and Townsend and Crew LLP (57) ABSTRACT

The present invention provides a process of identifying protooncogenes using high-throughput provirus tagging (HPT), e.g., by recovering host/virus junction sequences from chimeric transcripts containing both host and virus sequences.

5 Claims, 8 Drawing Sheets

FIG. 1

Figure 1:
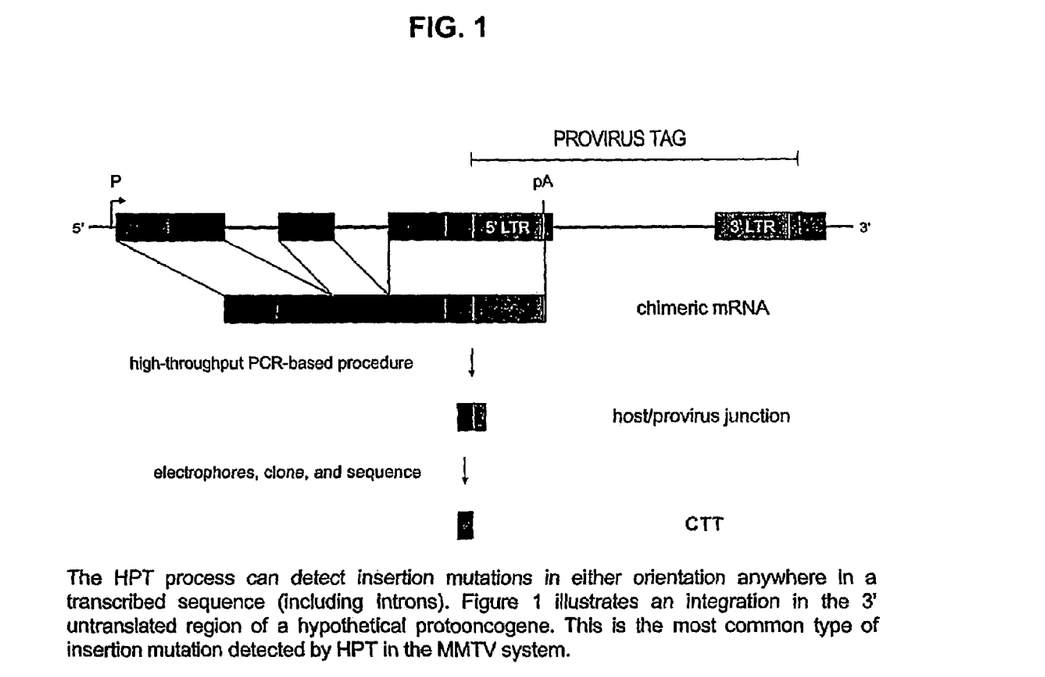
FIG. 1 shows a conceptual diagram of the methods of the invention.

The HPT process can detect insertion mutations in either orientation anywhere in a transcribed sequence (including introns). Figure 1 illustrates an integration in the 3' untranslated region of a hypothetical protooncogene. This is the most common type of insertion mutation detected by HPT in the MMTV system.

| LANE | TUMOR | RESULT | LANE | TUMOR | RESULT | LANE | TUMOR | RESULT | LANE | TUMOR | RESULT |
|---|---|---|---|---|---|---|---|---|---|---|---|
| 1 | MM0001 | Wnt3 | 13 | MM0033 | – | 25 | MM0046 | – | 37 | MM0084 | Sp100 |
| 2 | MM0002 | – | 14 | MM0034 | Fgf3 | 26 | MM0047 | – | 38 | MM0085 | – |
| 3 | MM0003 | Fgf3 | 15 | MM0035 | – | 27 | MM0048 | – | 39 | MM0091 | – |
| 4 | MM0004 | – | 16 | MM0036 | – | 28 | MM0049 | – | 40 | MM0092 | Wnt3a |
| 5 | MM0005 | – | 17 | MM0037 | – | 29 | MM0064 | novel | 41 | MM0093 | – |
| 6 | MM0006 | Fgf8 | 18 | MM0038 | Myb | 30 | MM0065 | novel | 42 | MM0094 | Fgf3 |
| 7 | MM0007 | – | 19 | MM0039 | – | 31 | MM0066 | – | 43 | MM0095 | – |
| 8 | MM0008 | – | 20 | MM0040 | – | 32 | MM0074 | – | 44 | MM0097 | – |
| 9 | MM0009 | Ins2/Igf2 | 21 | MM0041 | – | 33 | MM0077 | – | 45 | MM0099 | – |
| 10 | MM0010 | novel | 22 | MM0042 | – | 34 | MM0078 | unusable | 46 | MM0103 | novel |
| 11 | MM0011 | – | 23 | MM0044 | – | 35 | MM0080 | – | 47 | MM0134 | Wnt1 |
| 12 | MM0029 | Fgf3 | 24 | MM0045 | unusable | 36 | MM0081 | – | 48 | MM0250 | unusable |

FIG. 4A

CTTs FROM FIGURE 3

| CTT | SAMPLE | BAND | SIZE | BLAST RESULTS |
|---|---|---|---|---|
| CTT0001 | MM0001 | A | 101 | Wnt3 |
| CTT0002 | MM0003 | A | 75 | Fgf3 |
| CTT0003 | MM0006 | A | 46 | Fgf8 |
| CTT0004 | MM0009 | A | 18 | Ins2/Igf2 |
| CTT0005 | MM0010 | A | 79 | novel |
| CTT0006 | MM0029 | A | 51 | Fgf3 |
| CTT0007 | MM0034 | A | 260 | Fgf3 |
| CTT0008 | MM0038 | A | 45 | Myb |
| CTT0009 | MM0045 | A | 31 | unusable |
| CTT0010 | MM0064 | A | 46 | novel |
| CTT0011 | MM0065 | A | 201 | novel |
| CTT0012 | MM0078 | A | 2 | unusable |
| CTT0013 | MM0084 | A | 122 | Sp100 |
| CTT0014 | MM0084 | B | 16 | unusable |
| CTT0015 | MM0092 | A | 22 | Wnt3a |
| CTT0016 | MM0094 | A | 322 | Fgf3 |
| CTT0017 | MM0103 | A | 48 | novel |
| CTT0018 | MM0134 | A | 158 | Wnt1 |
| CTT0019 | MM0250 | A | 2 | unusable |

CTT0001

CATGGCGAGA TTCTGTGTCC AAGCTGCCTC TACTCGTGAC ATTCCAAGAT GCCTCTGAGG
TGGGAACTGT GAAATAGGAC AGAGCCCCAC AGTCCCCTCT T

CTT0002

CATGGCAAGA TGGAGACTTT GTCTACCAGG GCCACTCCAA GCACCCAGCT GCATACAGGT
GGACTGGCTG TGGCC

CTT0003

CATGCTGGCT GTTCCTGCAG CCCAGCTACT GGGACAATCT GGAAAC

FIG. 4B

CTT0004

CATGTGCTCA ATCCATAG

---

CTT0005

CATGGGTCCC TGAAGGGTCT CTCCTTTAGC AAACCCCTGT ACAGTTGAAG TGATTTTTCA
GGTACCCATT GGTCTTAGC

---

CTT0006

CATGGCAAGA TGGAGACTTT GTCTACCAGG GCCACTCCAA GCACCCAGCT G

---

CTT0007

CATGCACACA AACTGGCCCT GAACTTTTGA CTTCCAGGCC TCTGCCTCTC TGCGCGCACA
CACACACTCG CACTCCTGTA TATGAAGCGT ATATGTGTTT CTCTGGGAAC TGTTTTTATC
AGGTGAAGTA CTTCCTTTGT TCTTGCTACC CACCTCCAGG GCTCCAGGAT CTCCAGACAG
CCAACCCTAA GACAGGCCCA GCTTCTCTGT ATCTCTGTGA TGAGAACCTT GGCATAGAGC
TGCCTCACCC TCGGGATAGG

---

CTT0008

CATGCCTCTG GAAAGTACCT TAAACATAGA ATCCCCTCCC TAGTG

---

CTT0009

CATGGTTTTT TTTTTTTTGA GTGTGTGTGT G

---

CTT0010

CATGCAGATT AAAGTACATA TATGTAAAAA ATAAAAATAA ATCTTT

---

CTT0011

CATGATAAGG TTAGAGTTTT GTGAGCCTCC TTAACCTTGC TCAGCAAGCG TTGGGCTCTT
GGCAGCCGAG CTGCCATCTT TCTCATCCCC GATAGAGCCA GCCGCCCTTG TCGTGTCTTG
AATAAGTTAG AGGAGGCATT ATAGAGCGGA CCTAAACATT TGCCTTGGAG CCTGAGGGAT

FIG. 4C

GGGGATTGGC TGAATGTGAA T

---

CTT0012

CA

---

CTT0013

CATGAATTCA TCACTGGTAA AATGTATGAA TTTCTTCTGA GACAGAGTCT TCTTATTGGC
TTACACTTGC TTCGAGCGGA TGATTCTGCT GCTTCAGCCT CTTGAGATGC TCAGATATGT
GC

---

CTT0014

CATGGATGCT ATTGGG

---

CTT0015

CATGAGAGGG TGCTTCAGGG TG

---

CTT0016

CATGCACACA AACTGGCCCT GAACTTTTGA CTTCCAGGCC TCTGCCTCTC TGCGCGCACA
CACACACTCG CACTCCTGTA TATGAAGCGT ATATGTGTTT CTCTGGGAAC TGTTTTTATC
AGGTGAAGTA CTTCCTTTGT TCTTGCTACC CACCTCCAGG GCTCCAGGAT CTCCAGACAG
CCAACCCTAA GACAGGCCCA GCTTCCTCTG TATCTCTGTG ATGAGAACCT TGGCATAGAG
CTGCCCTCAC CCTCGGGATA GGGCTTATGT TCCCCGGAAC GAGCCAGGCA CCTCAACAGC
TCCTGGGGAG GAATAGGGGA CT

---

CTT0017

CATGAATTCC ACACCTCCAT CAAGGGTGTC TTCTCCAGTG AGCCCCGG

---

CTT0018

CATGCCTCCC TCAGCCTCCT CCCACCCCTT CCTGTCCTGC CTCCTCATCA CTGTGTAAAT
AATTTGCACC GAAATGTGGC CGCAGAGCCA CGCGTTCGGT TATGTAAATA AAACTATTTA
TTGTGCTGGG TTCCAGCCTG GGTTGCAGAG ACCACCCT

FIG. 4D

CTT0019

NEW CANDIDATE PROTOONCOGENES

This group includes all novel CTT sequences ≥ 20 bp. Additional sequences are pending.

| CTT LOCUS | SAMPLE | BAND | SIZE |
|---|---|---|---|
| CTT0005 | MM0010 | A | 79 |
| CTT0010 | MM0064 | A | 46 |
| CTT0011 | MM0065 | A | 201 |
| CTT0017 | MM0103 | A | 48 |
| CTT0020 | MM0154 | A | 68 |

CTT0005
See Figure 4B

CTT0010
See Figure 4B

CTT0011
See Figure 4 B-4C

CTT0017
See Figure 4C

CTT0020

CATGCTAATG GAGTTTATTC TTAGGACTGC CTCCTGCATC CATTGATTGA CTTAAATATG TGCACACT

SEQUENCE LISTING

```
<160> NUMBER OF SEQ ID NOS: 18

<210> SEQ ID NO 1
<211> LENGTH: 101
<212> TYPE: DNA
<213> ORGANISM: Mouse

<400> SEQUENCE: 1
catggcgaga ttctgtgtcc aagctgcctc tactcgtgac attccaagat gcctctgagg      60
tgggaactgt gaaataggac agagccccac agtcccctct t                        101

<210> SEQ ID NO 2
<211> LENGTH: 75
<212> TYPE: DNA
<213> ORGANISM: Mouse

<400> SEQUENCE: 2
catggcaaga tggagacttt gtctaccagg gccactccaa gcacccagct gcatacaggt      60
ggactggctg tggcc                                                      75

<210> SEQ ID NO 3
<211> LENGTH: 46
<212> TYPE: DNA
<213> ORGANISM: Mouse

<400> SEQUENCE: 3
catgctggct gttcctgcag cccagctact gggacaatct ggaaac                    46
```

```
<210> SEQ ID NO 4
<211> LENGTH: 18
<212> TYPE: DNA
<213> ORGANISM: Mouse

<400> SEQUENCE: 4
catgtgctca atccatag                                                18

<210> SEQ ID NO 5
<211> LENGTH: 79
<212> TYPE: DNA
<213> ORGANISM: Mouse

<400> SEQUENCE: 5
catgggtccc tgaagggtct ctcctttagc aaacccctgt acagttgaag tgattttca   60 ggtacccatt ggtcttagc                                               79

<210> SEQ ID NO 6
<211> LENGTH: 51
<212> TYPE: DNA
<213> ORGANISM: Mouse

<400> SEQUENCE: 6
catggcaaga tggagacttt gtctaccagg gccactccaa gcacccagct g            51

<210> SEQ ID NO 7
<211> LENGTH: 260
<212> TYPE: DNA
<213> ORGANISM: Mouse

<400> SEQUENCE: 7
catgcacaca aactggccct gaacttttga cttccaggcc tctgcctctc tgcgcgcaca   60
cacacactcg cactcctgta tatgaagcgt atatgtgttt ctctgggaac tgtttttatc  120
aggtgaagta cttcctttgt tcttgctacc cacctccagg gctccaggat ctccagacag  180
ccaaccctaa gacaggccca gcttctctgt atctctgtga tgagaacctt ggcatagagc  240
tgcctcaccc tcgggatagg                                              260

<210> SEQ ID NO 8
<211> LENGTH: 45
<212> TYPE: DNA
<213> ORGANISM: Mouse

<400> SEQUENCE: 8
catgcctctg gaaagtacct taaacataga atccctccc tagtg                   45

<210> SEQ ID NO 9
<211> LENGTH: 31
<212> TYPE: DNA
<213> ORGANISM: Mouse

<400> SEQUENCE: 9
catggttttt ttttttttga gtgtgtgtgt g                                 31

<210> SEQ ID NO 10
<211> LENGTH: 46
<212> TYPE: DNA
<213> ORGANISM: Mouse

<400> SEQUENCE: 10
catgcagatt aaagtacata tatgtaaaaa ataaaaataa atcttt                 46
```

<210> SEQ ID NO 11
<211> LENGTH: 201
<212> TYPE: DNA
<213> ORGANISM: Mouse

<400> SEQUENCE: 11
catgataagg ttagagtttt gtgagcctcc ttaaccttgc tcagcaagcg ttgggctctt    60
ggcagccgag ctgccatctt tctcatcccc gatagagcca gccgcccttg tcgtgtcttg   120
aataagttag aggaggcatt atagagcgga cctaaacatt tgccttggag cctgagggat   180
ggggattggc tgaatgtgaa t                                             201

<210> SEQ ID NO 12
<211> LENGTH: 122
<212> TYPE: DNA
<213> ORGANISM: Mouse

<400> SEQUENCE: 12
catgaattca tcactggtaa aatgtatgaa tttcttctga gacagagtct tcttattggc    60
ttacacttgc ttcgagcgga tgattctgct gcttcagcct cttgagatgc tcagatatgt   120
gc                                                                  122

<210> SEQ ID NO 13
<211> LENGTH: 16
<212> TYPE: DNA
<213> ORGANISM: Mouse

<400> SEQUENCE: 13
catggatgct attggg                                                    16

<210> SEQ ID NO 14
<211> LENGTH: 22
<212> TYPE: DNA
<213> ORGANISM: Mouse

<400> SEQUENCE: 14
catgagaggg tgcttcaggg tg                                             22

<210> SEQ ID NO 15
<211> LENGTH: 322
<212> TYPE: DNA
<213> ORGANISM: Mouse

<400> SEQUENCE: 15
catgcacaca aactggccct gaacttttga cttccaggcc tctgcctctc tgcgcgcaca    60
cacacactcg cactcctgta tatgaagcgt atatgtgttt ctctgggaac tgtttttatc   120
aggtgaagta cttcctttgt tcttgctacc cacctccagg gctccaggat ctccagacag   180
ccaaccctaa gacaggccca gcttcctctg tatctctgtg atgagaacct tggcatagag   240
ctgccctcac cctcgggata gggcttatgt tccccggaac gagccaggca cctcaacagc   300
tcctggggag gaataggggga ct                                           322

<210> SEQ ID NO 16
<211> LENGTH: 48
<212> TYPE: DNA
<213> ORGANISM: Mouse

<400> SEQUENCE: 16
catgaattcc acacctccat caagggtgtc ttctccagtg agccccgg                 48

-continued

```
<210> SEQ ID NO 17
<211> LENGTH: 158
<212> TYPE: DNA
<213> ORGANISM: Mouse

<400> SEQUENCE: 17
catgcctccc tcagcctcct cccacccctt cctgtcctgc ctcctcatca ctgtgtaaat      60
aatttgcacc gaaatgtggc cgcagagcca cgcgttcggt tatgtaaata aaactattta    120
ttgtgctggg ttccagcctg ggttgcagag accaccct                             158

<210> SEQ ID NO 18
<211> LENGTH: 68
<212> TYPE: DNA
<213> ORGANISM: Mouse

<400> SEQUENCE: 18
catgctaatg gagtttattc ttaggactgc ctcctgcatc cattgattga cttaaatatg      60
tgcacact                                                               68
```

HIGH THROUGH-PUT CLONING OF PROTOONCOGENES

This application is the FIRST submission concerning a filing under 35 U.S.C. 371, claiming the benefit of priority to PCT patent application Ser. No. PCT/US02/01651, filed Jan. 18, 2002, which claims priority to U.S. provisional patent application No. 60/262,724, filed Jan. 18, 2001.

BACKGROUND OF THE INVENTION

Cancer is the phenotypic manifestation of a complex biological progression during which cells accumulate multiple somatic mutations, eventually acquiring sufficient growth autonomy to metastasize. Although inherited cancer susceptibility alleles and epigenetic factors influence the process, carcinogenesis is fundamentally driven by somatic cell evolution (i.e., mutation and natural selection of variants with progressive loss of growth control). The genes which are the targets of these somatic mutations are classified as either protooncogenes or tumor suppressor genes, depending on whether their mutant phenotyes are dominant or recessive, respectively.

In several animal models, an important source of protooncogene somatic mutations is retrovirus infection. Retroviruses cause can cause cancer by essentially three mechanisms: (i) transduction of host protooncogenes (which then become viral oncogenes), (ii) trans-acting effects of viral gene products, or (iii) cis-acting effects of provirus integration on protooncogenes at or very near the site of integration. In the later case, only rare infected cells are affected. This phenomenon is called provirus insertion mutation, and will be discussed in detail in the following narrative.

As a normal consequence of the retroviral life-cycle, DNA copies of the retrovirus genome (called a proviruses) are integrated into the host genome. Accordingly, retroviruses are obligate mutagens. A newly-integrated provirus can affect gene expression in cis at or near the integration site by one of two mechanisms. Type I insertion mutations up-regulate transcription of proximal genes as a consequence of regulatory sequences (enhancers and/or promoters) within the proviral long terminal repeats (LTRs). These insertion mutations typically affect genes that are not expressed in the target tissue. Type II insertion mutations cause truncation of coding regions due to either integration directly within an open reading frame or integration within an intron upstream of the stop codon.

Provirus integration is random. Therefore, all host genes are targets of insertion mutation. In a chronically-infected tissue, a sufficient number of cells have new provirus insertions that, statistically, all genes in the genome are mutated. In rare cases, an insertion mutation will "activate" a host protooncogene, providing the affected cell with a dominant selective growth advantage in vivo. If the cell progresses to cancer, then the protooncogene insertion mutation will be present at clonal stoichiometry in the tumor. Such "clonally-integrated" proviruses serve to "tag" the locations of protooncogenes in the genome. In cases where the proviral enhancer is responsible for dysregulation of the mutated protooncogene, the provirus can be 100 kb or more from the site of integration (but usually much closer).

This relatively tight linkage between clonally-integrated proviruses and protooncogenes is the basis for a classical experimental strategy, called "provirus tagging," in which slow-transforming retroviruses that act by an insertion mutation mechanism are used to isolate protooncogenes. The complete logic is as follows: (i) uninfected animals have low cancer rates, (ii) infected animals have high cancer rates, (iii) the retroviruses involved do not carry transduced host protooncogenes or pathogenic trans-acting viral genes, (iv) the cancer incidence must therefore be a direct consequence of provirus integration effects on host protooncogenes, (v) since provirus integration is random, rare integrants will "activate" host protooncogenes that provide a selective growth advantage, and (vi) these rare events result in new proviruses at clonal stoichiometries in tumors.

In contrast to mutations caused by chemicals, radiation, or spontaneous errors, protooncogene insertion mutations can be easily located by virtue of the fact that a convenient-sized genetic marker of known sequence is present at the site of mutation (i.e., the provirus). Host sequences that flank clonally-integrated proviruses can be recovered using a variety of molecular techniques. Once these sequences are in hand, the tagged protooncogenes can be subsequently identified.

There are two unequivocal biological criteria that provide prima facie evidence that a protooncogene is present at or very near a proviral integration site. The first criterion is the presence of provirus at the same locus in two or more independent tumors. This is because the genome is too large for random integrations to result in observable clustering. Any clustering that is detected is indirect evidence for biological selection (i.e., the tumor phenotype resulting from activation of a host protooncogene). The second criterion is a tumor with only a single insertion mutation. In this case, if there is only one insertion mutation, then that provirus is located at a protooncogene locus. If either of these criteria are met, sufficient evidence exists to reach a conclusion that a protooncogene locus has been located.

The provirus tagging concept has withstood two decades of testing in many retrovirus tumor models that have a provirus insertion mutation etiology. The biological logic is so compelling, and the experimental results so unequivocal, that the claim can be made that the activated genes are functionally-validated as protooncogenes at the time of discovery. Formal confirmation typically involves isolation of a full-length cDNA for use in a bioassay (either a cell-based transformation assay or transgenic mice).

Provirus tagging in avian and mammalian systems has led to the identification of approximately 50–60 protooncogenes (many of which were new genes not previously identified by other techniques). The three mammalian retroviruses that cause cancer by an insertion mutation mechanism are FeLV (leukemia/lymphoma in cats), MLV (leukemia/lymphoma in mice and rats), and MMTV (mammary cancer in mice).

Despite the tremendous promise of the provirus tagging approach, as originally designed it was not well-suited for large scale application. The main problem was that it was too laborious and, therefore, the risks of reisolating known genes became unacceptable for most investigators. As a consequence, the protooncogene discovery potential of this approach has remained largely untapped.

BRIEF SUMMARY OF THE INVENTION

Recognizing this untapped potential, we designed and implemented HPT to overcome the limitations of the original provirus tagging approach (which were all fundamentally related to throughput). We were able to successfully increase provirus tagging throughput to the point where reisolation of known loci is no longer a problem. In fact, this is now a desirable outcome because it serves as an "internal control" that helps validate the biological relevance of the new genes that are recovered in parallel.

As a functional oncogenomics strategy, HPT has many advantages. First, it is a functional cloning rather than brute-force (e.g., differential display-based) approach; and the genes that are recovered are functionally-validated at the time of discovery. Second, it has high biological relevance since protooncogenes are isolated directly from clinical material (rather than from cell lines, transplants, or materials generated by gene transfer). Third, it is amenable to automation, meaning that throughput and time-to-discovery is a simple function of research resources.

Figure 2:
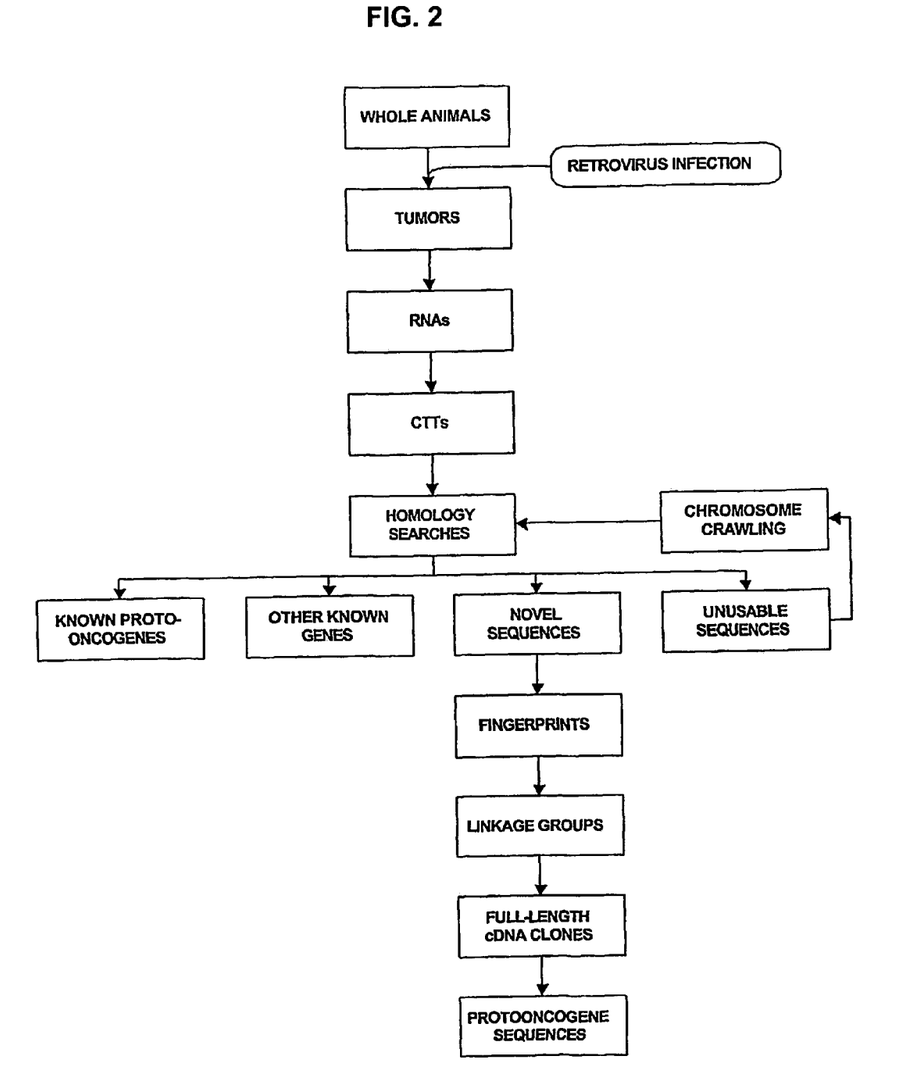
FIG. 2 shows a flow chart of the methods of the invention.

The invention is a process called high-throughput provirus tagging (HPT). HPT yields partial protooncogene cDNAs from retrovirus-induced tumors. Using these partial cDNAs, conventional techniques can be used to recover full-length cDNAs (we have not yet performed this final step). A conceptual diagram is shown in FIG. 1 and a flow chart of the process is shown in FIG. 2.

HPT is derived from classical procedures for provirus tagging. It is specific for tumors induced by retroviruses that cause cancer via a provirus insertion mutation mechanism. This subset of retroviruses includes the mouse mammary tumor virus (MMTV). MMTV-induced tumors were used to implement the HPT process.

In tumors induced by provirus insertion mutation, new proviral integrants present at clonal stoichiometries tag the locations of host protooncogenes. The majority of such integrants fall outside of transcribed regions. However, a subset fall within sequences that are transcribed, and result in the formation of chimeric transcripts containing both host and virus sequences. HPT is designed to recover host/virus junction sequences from these chimeric transcripts.

The strategy used is a modified/optimized anchored-PCR (A-PCR) approach incorporating a custom anchor. The procedure amplifies host sequences upstream of 5' LTRs. If a transcript containing a host/virus junction is present in a tumor, then a unique fragment is generated by the A-PCR procedure, which can be detected by gel electrophoresis. In addition, one or more common fragments will be generated from retroviral transcripts that contain the 5' end of the 3' LTR.

The innovation that makes this approach feasible is that cDNAs are digested with a restriction enzyme with a 4 bp recognition sequence prior to amplification. This generates populations of target cDNAs that (1) have precise 5' ends, and (2) are sufficiently small to ensure that they will efficiently amplify. In addition, restriction enzymes are selected that produce the largest possible retroviral transcription products (so that they run at the top of the gel). This is critical because chimeric transcripts are present at much lower levels than the major retroviral transcripts. By selection of appropriate restriction enzymes, a large detection window is available in a region of the gel where the signal-to-noise ratio is most favorable. In addition, during amplification, cycling times are ramped to favor smaller products.

The provirus tagging strategy has been used for almost 20 years. It is a DNA-based detection method where identification of new genes requires positional cloning procedures to find genes adjacent to integration sites recovered from tumor DNA. This laborious process has been recently improved by PCR procedures. Nevertheless, unless the integration falls within known sequence, it is not possible to identify the affected gene without a large amount of additional work.

The advantage of HPT is that it is the first PCR-based provirus tagging approach that recovers protooncogenes from RNA. Because RNA is used, new protooncogenes are identified directly. Although only a fraction of tumors have insertion mutations that generate a chimeric transcript, the process has been designed to be high-throughput. As a consequence, the fact that most samples are non-informative is not a problem. In addition, the process is so efficient that recovery of know protooncogenes does not represent an unacceptable loss of effort, and, in fact, serves as an internal control to verify the robustness of the strategy.

DETAILED DESCRIPTION OF THE INVENTION

A. General Purpose or Utility

HPT is new technology for isolating partial cDNAs representing functionally validated protooncogenes. It is a scaleable batch process that is amenable to high-throughput applications. Saturation mutagenesis of all accessible protooncogenes in the mammalian genome is feasible using HPT.

B. Brief Description of the State of the Art Prior to your Invention

The state-of-the-art prior to this invention was PCR-based isolation of provirus integration sites from tumor DNA. This method, as currently practiced, involves an inverse-PCR (I-PCR strategy). Identification of the activated protooncogene at a particular integration locus relies on prior characterization of the gene by other methods. For novel genes, positional cloning is required. The DNA-based method involves considerable risk, since it is not know until the end of the positional cloning process whether the locus under investigation is novel.

C: Technical Description
1. Isolate total RNA from frozen tumor tissue.
2. Treat with DNase.
3. Prepare double stranded cDNA.
4. Digest with restriction enzyme.
5. Ligate anchor to digested cDNA.
6. PCR amplify targets with LTR and anchor primers.
7. Reamplify targets with nested LTR and anchor primers.
8. Electrophores amplification products.
9. Sample new band, if present.
10. Reamplify band.
11. Clone.
12. Determine sequence.
13. Assign CTT number.
14. Perform homology search.
15. If sequence is anonymous, design primers for fingerprinting.
16. Use primers to amplify BAC and YAC superpools.
17. Electrophores to determine banding pattern for the locus (fingerprint).
18. Assemble into linkage groups.

CTTs can be assembled into linkage groups based on their fingerprints. Using a representative CTT from each linkage group, conventional techniques can then be used to isolate full-length cDNAs for sequence analysis and deduction of the amino acid sequencing of the protooncogene.

D. Practicing the Invention

Figure 3:
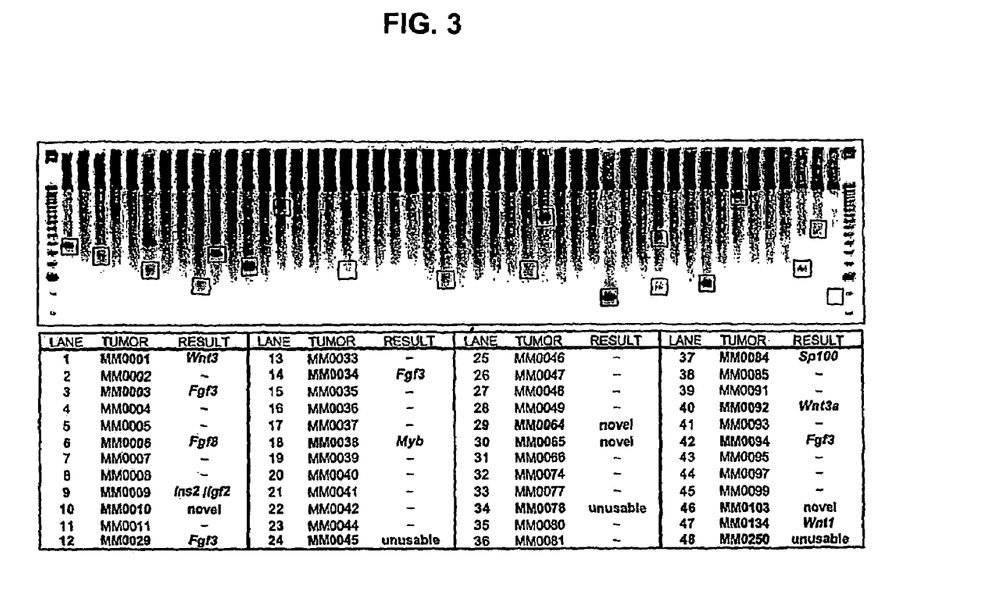
FIG. 3 shows an example of HPT screening data.
Figure 4A:
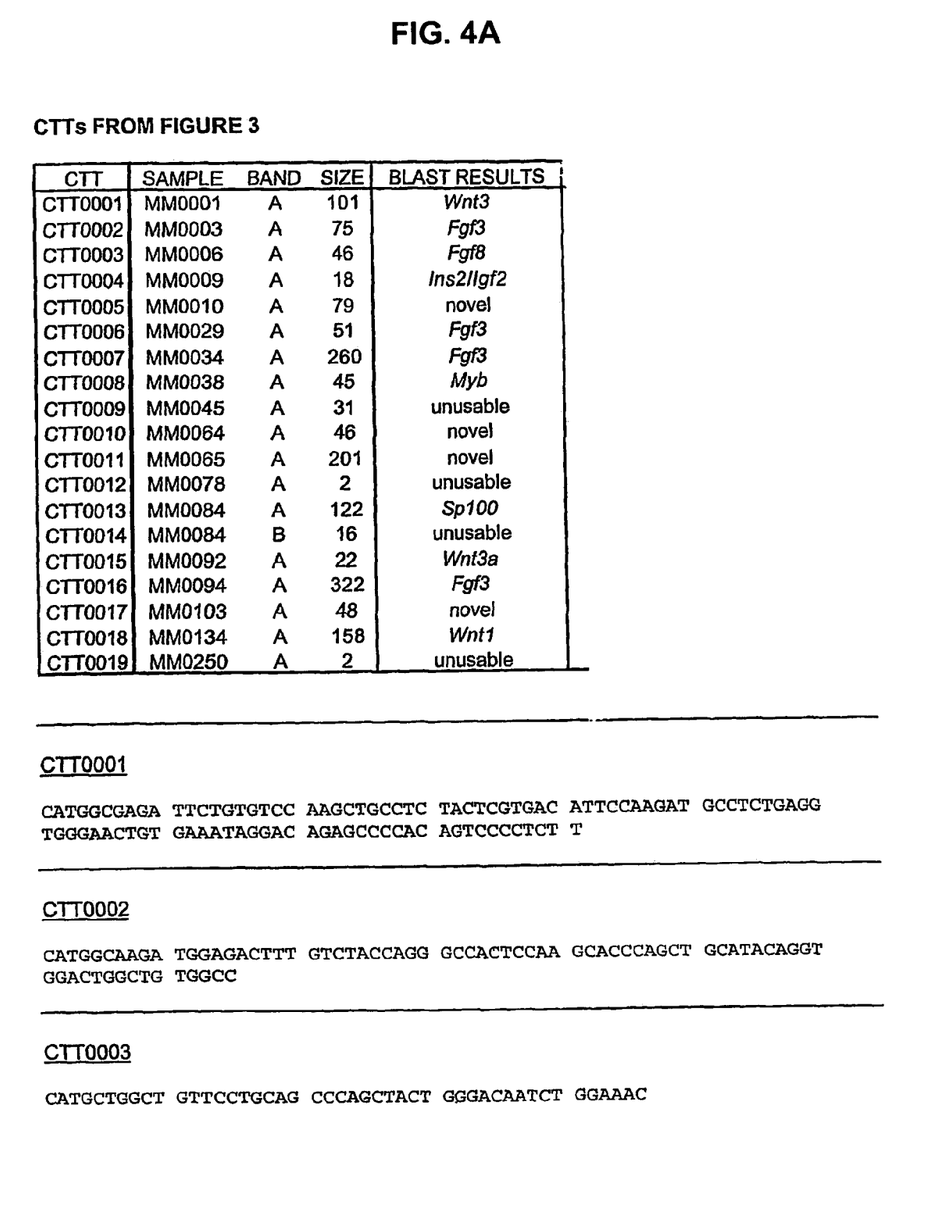
FIG. 4 shows CTTs from FIG. 3.
Figure 4B:
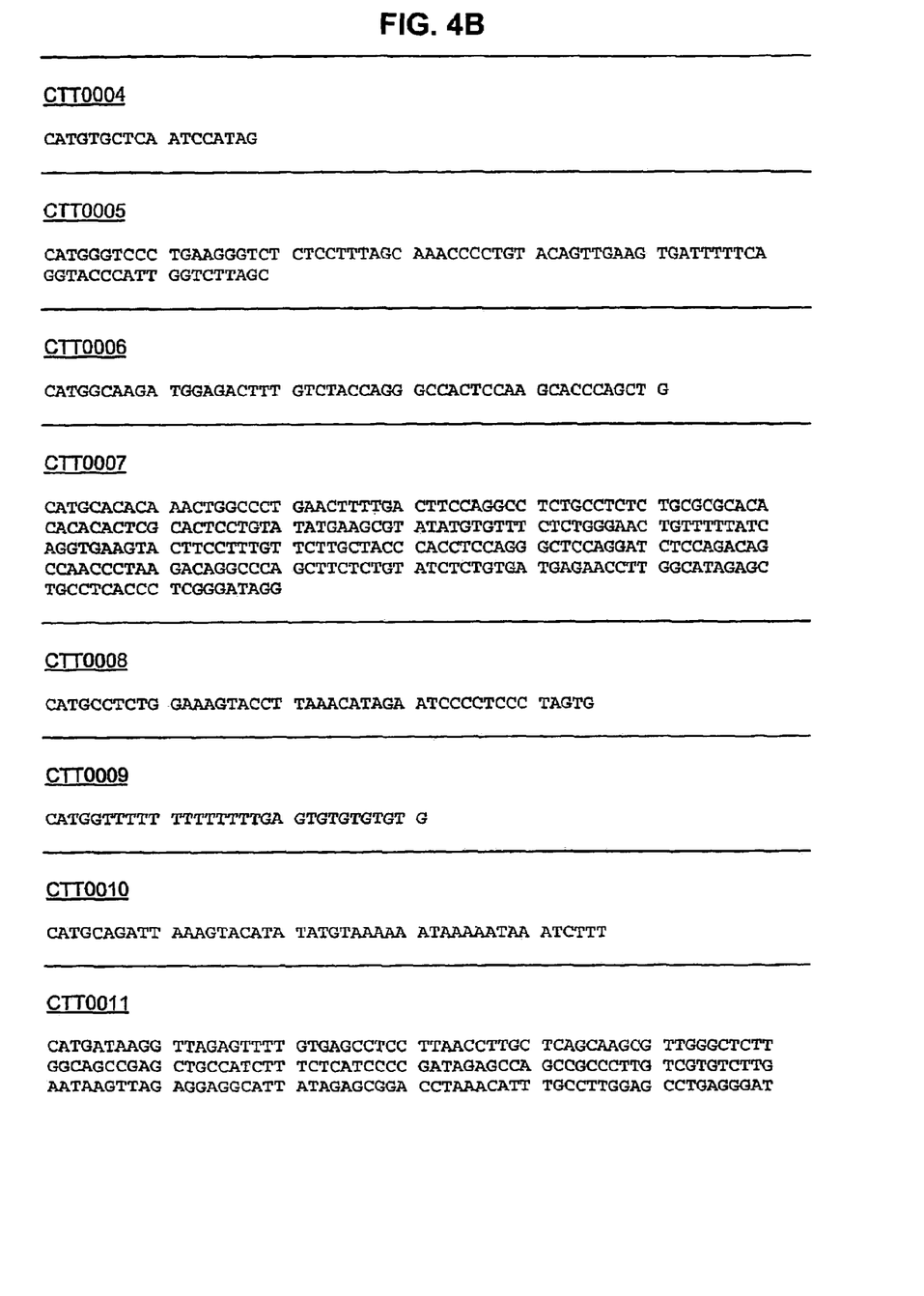
Figure 4C:
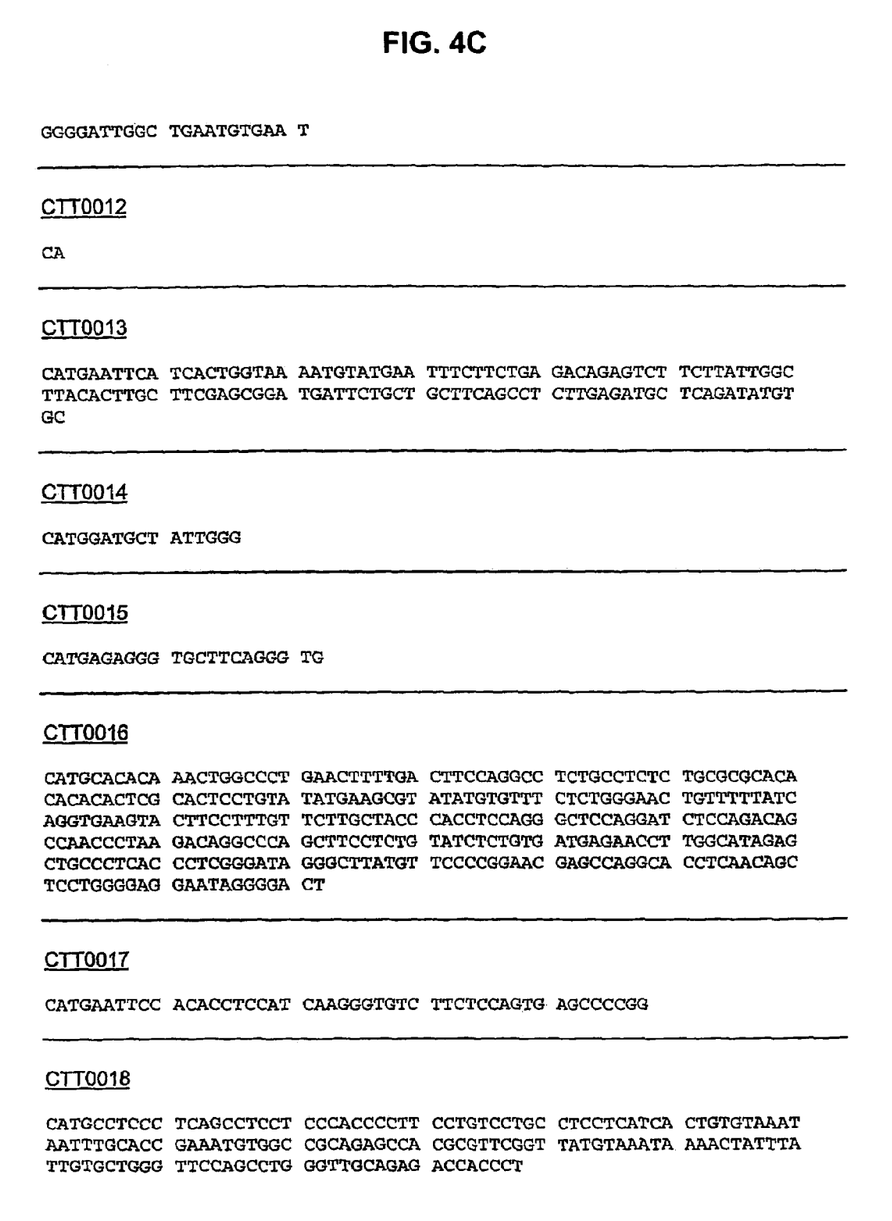
Figure 4D:
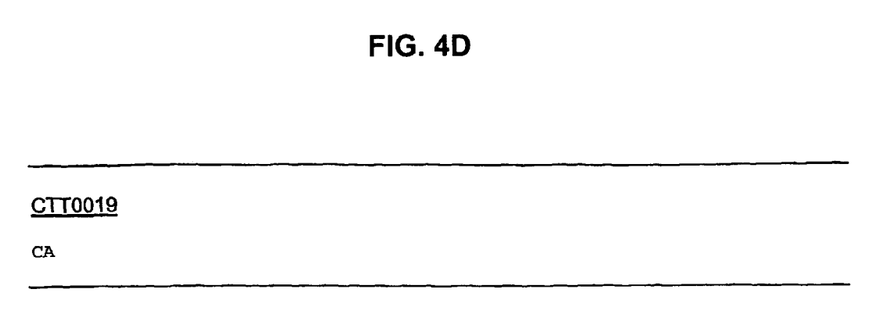
Figure 5:
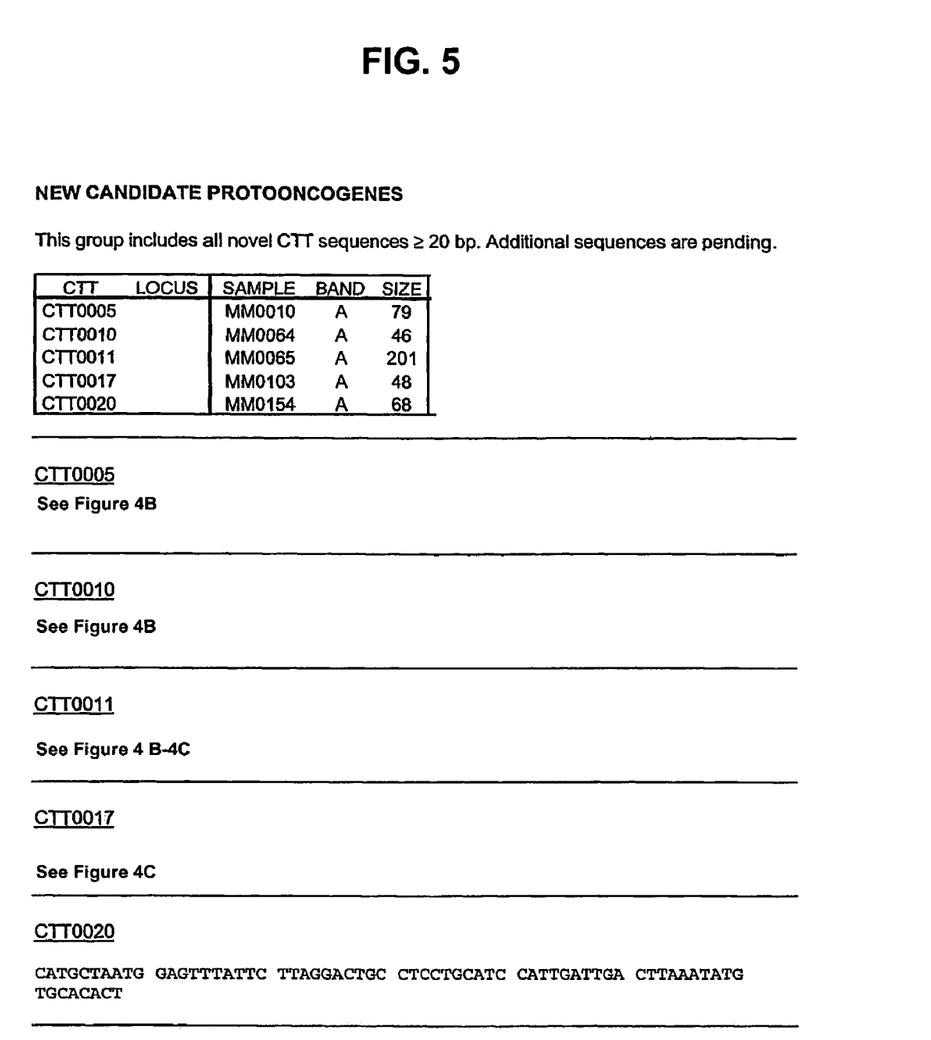
FIG. 5 shows new candidate protooncogenes.

Shown are the A-PCR results from an HPT analysis of 48 independent MMTV-induced tumors performed as described in the previous sections. Tabulated below the gel are the results of a BLAST search using the CTT from each recovered junction fragment (boxes). In addition to novel sequences, known targets of MMTV-insertion mutation were recovered. Also recovered, were known protooncogenes not previously recognized as targets of MMTV and know genes that had not previously been known to have protooncogene function. The processing time from frozen tissue to cDNA sequence is five work days.

E. Possible Modifications and Variations on the Best Way

1. A partial digestion strategy is being implemented to recover more chimeric transcript sequence from loci which have CTTs that are too short to BLAST and/or contain low complexity or repetitive sequences. This will allow usable sequence to be recovered upstream of most CTTs currently listed as "unusable".

2. The HPT process has been implemented to recover host/virus junction fragments from integrants in the same transcriptional orientation as the target gene using minus strand primers from the 5' LTR. It is also possible to modify the procedure to recover host/virus junctions from integrants in the opposite orientation using plus strand primers from the 3' LTR.

3. The current procedure generates retroviral transcripts that run high in the get so that novel host/virus junctions are clearly visible. It is also possible to remove, destroy, and/or inhibit the formation of retroviral transcripts.

4. The process claim can be generalized to include any method that uses a chimeric mRNA between a retrovirus and cellular gene to discover a gene of interest based on either an in vivo or cell culture bioassay.

F. Advantages and Improvements over Existing Practice

The primary advantage and improvement over the existing state of the art is that the affected protooncogene is specifically recovered by the HPT process. Using DNA-based approaches, positional cloning is required to find the protooncogenes at loci that have not previously been characterized.

The following features are believed to be new;

1. First cDNA-based application of provirus tagging using PCR methods.

Glossary

CTT chimeric transcript tag

HPT high-throughput protooncogene tagging

LTR long terminal repeat

MMTV mouse mammary tumor virus

All cited references are expressly incorporated herein by reference.

The invention claimed is:

1. A method of identifying a candidate protooncogene comprising:

inserting a provirus comprising a long terminal repeat (LTR) sequence into the genome of a host, thereby forming a junction site of DNA of said us provirus and said host;

isolating mRNA from said host; preparing cDNA from said mRNA;

digesting said cDNA with a restriction enzyme, thereby producing a plurality of cDNA fragments;

ligating an anchor to an end of each cDNA fragment;

amplifying said cDNA fragments using an LTR-specific primer and an anchor-specific primer to identify the nucleic acid sequence of said junction site, whereby said candidate protooncogene is identified.

2. The method of claim 1, wherein said LTR is a 5' LTR.

3. The method of claim 1, wherein said LTR is a 3' LTR.

4. The method of claim 1, wherein said candidate protooncogene is identified by isolating a full length cDNA molecule.

5. The method of claim 1, wherein said restriction enzyme has a 4 base pair recognition sequence.

* * * * *